(12) United States Patent
Iida et al.

(10) Patent No.: US 12,048,563 B2
(45) Date of Patent: Jul. 30, 2024

(54) ON-BED STATE MONITORING SYSTEM AND BED INCLUDING SAME

(71) Applicant: Minebea Mitsumi Inc., Nagano (JP)

(72) Inventors: Norihito Iida, Sagamihara (JP); Toshiaki Nishimura, Kokubunji (JP)

(73) Assignee: MINEBEA MITSUMI Inc., Nagano (JP)

(*) Notice: Subject to any disclaimer, the term of this patent is extended or adjusted under 35 U.S.C. 154(b) by 0 days.

(21) Appl. No.: 16/957,164

(22) PCT Filed: Dec. 26, 2018

(86) PCT No.: PCT/JP2018/047899
§ 371 (c)(1),
(2) Date: Aug. 25, 2020

(87) PCT Pub. No.: WO2019/131781
PCT Pub. Date: Jul. 4, 2019

(65) Prior Publication Data
US 2021/0244361 A1    Aug. 12, 2021

(30) Foreign Application Priority Data
Dec. 28, 2017  (JP) .................................. 2017-252848

(51) Int. Cl.
*A61B 5/00* (2006.01)
*A61B 5/08* (2006.01)
*A61B 5/11* (2006.01)

(52) U.S. Cl.
CPC .......... *A61B 5/6892* (2013.01); *A61B 5/0816* (2013.01); *A61B 5/1121* (2013.01);
(Continued)

(58) Field of Classification Search
CPC ..... A61B 5/6892; A61B 5/742; A61B 5/0816; A61B 5/746; A61B 5/1121; A61B 5/7405; A61B 2562/0252
See application file for complete search history.

(56) References Cited

U.S. PATENT DOCUMENTS 6,208,250 B1 *  3/2001  Dixon ................. A61G 7/0509
                                                340/572.1
8,279,057 B2   10/2012  Hirose
(Continued)

FOREIGN PATENT DOCUMENTS

CN     101472545 A    7/2009
CN     102458339 A    5/2012
(Continued)

OTHER PUBLICATIONS

International Search Report for corresponding International Application No. PCT/JP2018/047899 mailed Feb. 12, 2019.
(Continued)

*Primary Examiner* — Rex R Holmes
(74) *Attorney, Agent, or Firm* — Pearne & Gordon LLP

(57) ABSTRACT

A present-in-bed state monitoring system (100) configured to monitor a present-in-bed state of a subject on a bed (BD) includes: a plurality of load detectors (11, 12, 13, 14) configured to be provided on the bed or under legs of the bed to detect a load of the subject; a center of gravity position calculating unit (31) configured to calculate a center of gravity position of the subject based on the detected load of the subject; a waveform output unit (32) configured to output a waveform including a respiratory waveform of the subject based on a temporal variation of the calculated center of gravity position; a center of gravity position determining unit (332) configured to determine whether or not the center of gravity position is in an edge area of the bed; a body motion determining unit (331) configured to
(Continued)

determine whether or not the subject has a body motion based on the waveform including the respiratory waveform of the subject, the body motion being different from a respiration of the subject; and a notifying unit (5) configured to perform a notification about the present-in-bed state of the subject based on a determination result of the body motion determining unit and a determination result of the center of gravity position determining unit.

6 Claims, 9 Drawing Sheets

(52) U.S. Cl.
CPC .......... *A61B 5/7405* (2013.01); *A61B 5/742* (2013.01); *A61B 5/746* (2013.01); *A61B 2562/0252* (2013.01)

(56) References Cited

U.S. PATENT DOCUMENTS

| | | | |
|---|---|---|---|
| 8,838,411 B2 | 9/2014 | Kazuno et al. | |
| 9,119,566 B2 | 9/2015 | Sakai et al. | |
| 10,390,735 B2 | 8/2019 | Akatsu et al. | |
| 2003/0090383 A1 | 5/2003 | Conway | |
| 2005/0107722 A1* | 5/2005 | Ozaki | A61B 5/6887 600/587 |
| 2007/0261894 A1 | 11/2007 | Harish | |
| 2009/0260158 A1* | 10/2009 | Kazuno | G01G 19/445 5/600 |
| 2010/0231376 A1 | 9/2010 | Hirose | |
| 2012/0078573 A1 | 3/2012 | Kazuno et al. | |
| 2013/0178715 A1 | 7/2013 | Sakai et al. | |
| 2016/0270721 A1* | 9/2016 | Raymann | A61B 5/0205 |
| 2018/0146889 A1 | 5/2018 | Akatsu et al. | |
| 2018/0242918 A1* | 8/2018 | Kogure | A61B 5/6892 |

FOREIGN PATENT DOCUMENTS

| | | |
|---|---|---|
| CN | 103169475 A | 6/2013 |
| CN | 203074701 U | 7/2013 |
| CN | 103263261 A | 8/2013 |
| CN | 105877759 A | 8/2016 |
| CN | 105943277 A | 9/2016 |
| JP | 06-327653 A | 11/1994 |
| JP | 11-290394 A | 10/1999 |
| JP | 2004-096457 A | 3/2004 |
| JP | 4002905 B2 | 11/2007 |
| JP | 2008-212306 A | 9/2008 |
| JP | 2008-264338 A | 11/2008 |
| JP | 4829020 B2 | 11/2011 |
| JP | 4965904 B2 | 7/2012 |
| JP | 2014-180432 A | 9/2014 |
| JP | 2016-123848 A | 7/2016 |
| JP | 2017-010383 A | 1/2017 |
| JP | 2017-077451 A | 4/2017 |
| JP | 2017-205409 A | 11/2017 |

OTHER PUBLICATIONS

Written Opinion for corresponding International Application No. PCT/JP2018/047899 dated Feb. 12, 2019.
Decision to Grant a Patent for corresponding Japanese Application No. 2017-252848 (now Japanese Patent No. 6,534,729) dated Apr. 26, 2019 and English translation computer-generated from J-Plat Pat of the JPO (Japan Platform for Patent Information).
Yasuhiro Takemura; "Non-contact, non-restrained bed watch system", Video Information Medical, Series medical engineering cooperation, Walking through medical engineering collaboration (46th), Feb. 1, 2014.
Chinese Office Action dated Feb. 7, 2021 for corresponding Chinese Application No. 201880090497.7 and English translation.
Chinese Office Action dated Aug. 30, 2021 for corresponding Chinese Application No. 201880090497.7 and English translation.
Extended European Search Report dated Sep. 10, 2021 for corresponding European Application No. 18893699.1.

\* cited by examiner

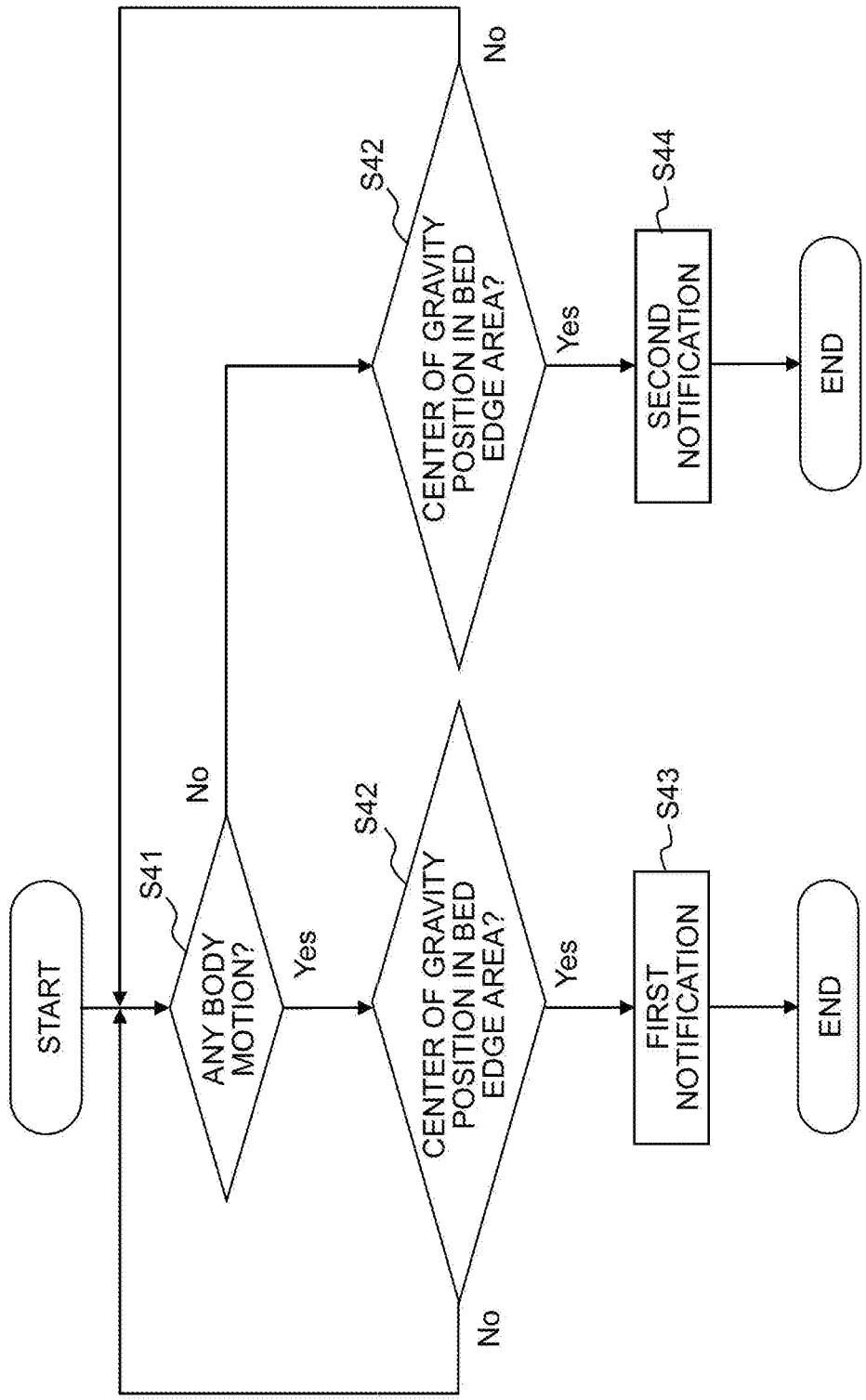

ON-BED STATE MONITORING SYSTEM AND BED INCLUDING SAME

CROSS-REFERENCE TO RELATED APPLICATIONS

This application is a National Stage of International Application No. PCT/JP2018/047899, filed on Dec. 26, 2018, which claims priority to Japanese Patent Application No. JP 2017-252848 which was filed on Dec. 28, 2017 and has been subsequently granted as a patent under number JP-6534729. The entireties of the aforementioned applications are herein incorporated by reference.

TECHNICAL FIELD

The present invention relates to a present-in-bed state monitoring system (on-bed state monitoring system) provided with a plurality of load detectors, and to a bed provided with the abovementioned system.

BACKGROUND ART

For the sites of medical treatment and caregiving, it is proposed to determine a state of a (human) subject on the basis of such a (body weight) load of the subject on a bed as detected by load detectors. In particular, for example, it is proposed to determine whether the subject is present in the bed or absent from the bed, estimate the respiratory rate of the subject, etc., on the basis of the detected load.

Patent Literature 1 discloses a method for detecting a present-in-bed situation for the bed to notify the information that the in-bed position of the subject is located in an end part area (edge area) of the bedding potion of the bed, on the basis of detecting of the load applied on the bedding portion of a bed with four load detecting means and a determining step carried out by fitting the load values outputted from the four load detecting means into a plurality of determination formulas.

CITATION LIST

Patent Literature 1: Japanese Patent No. 4965904

SUMMARY

Technical Problem

In the sites of medical treatment and caregiving, manpower is often not sufficient. Therefore, with the method for detecting a present-in-bed situation for the bed as disclosed in Patent Literature 1, it is desired to further prevent mistaken notifications.

An object of the present invention is to provide a present-in-bed state monitoring system and a bed provided with the abovementioned system capable of: determining a present-in-bed state of a subject on the bed with high precision, and notifying a user of the result determined above.

Solution to the Problem

According to a first aspect of the present invention, there is provided a present-in-bed state monitoring system configured to monitor a present-in-bed state of a subject on a bed, the system including:

a plurality of load detectors configured to be provided on the bed or under legs of the bed to detect a load of the subject;

a center of gravity position calculating unit configured to calculate a center of gravity position of the subject based on the detected load of the subject;

a waveform output unit configured to output a waveform including a respiratory waveform of the subject based on a temporal variation of the calculated center of gravity position;

a center of gravity position determining unit configured to determine whether or not the center of gravity position is in an edge area of the bed;

a body motion determining unit configured to determine whether or not the subject has a body motion based on the waveform including the respiratory waveform of the subject, the body motion being different from a respiration of the subject; and a notifying unit configured to perform a notification about the present-in-bed state of the subject based on a determination result of the body motion determining unit and a determination result of the center of gravity position determining unit.

The present-in-bed state monitoring system according to the first aspect may further include a notification control unit configured to cause the notifying unit to perform the notification based on the determination result of the body motion determining unit and the determination result of the center of gravity position determining unit, wherein the notification control unit may cause the notifying unit to perform a first notification in a case that the center of gravity position determining unit determines that the center of gravity position is in the edge area of the bed and the body motion determining unit determines that the subject has the body motion, and may cause the notifying unit to perform a second notification different from the first notification in a case that the center of gravity position determining unit determines that the center of gravity position is in the edge area of the bed and the body motion determining unit determines that the subject does not have the body motion.

In the present-in-bed state monitoring system according to the first aspect, the body motion determining unit may determine whether or not the subject has a large body motion involving a movement of a trunk of the subject, and the notification control unit may cause the notifying unit to perform the first notification in a case that the center of gravity position determining unit determines that the center of gravity position is in the edge area of the bed and the body motion determining unit determines that the subject has the large body motion.

In the present-in-bed state monitoring system according to the first aspect, the body motion determining unit may determine whether or not the subject has the body motion different from the respiration of the subject, based on an amplitude of the waveform including the respiratory waveform of the subject.

The present-in-bed state monitoring system according to the first aspect may further include a present-in-bed determining unit configured to determine whether or not the subject is present on the bed based on the respiratory waveform.

In the present-in-bed state monitoring system according to the first aspect, the notifying unit may include a monitor configured to perform the notification by an image, and a speaker configured to perform the notification by an audio.

According to a second aspect of the present invention, there is provided a bed system including a bed and the present-in-bed state monitoring system according to the first aspect.

Effects of the Invention

The present-in-bed state monitoring system and the bed provided with the abovementioned system according to the present invention can determine the present-in-bed state of the subject on the bed with high precision, and can notify a user of the result determined above.

BRIEF DESCRIPTION OF THE DRAWINGS

FIG. 6 is a flow chart depicting a procedure of a present-in-bed state monitoring step.

DESCRIPTION OF EMBODIMENT

Embodiment

Referring to FIGS. 1 to 8, an explanation will be made on an embodiment of the present invention.

Figure 1:
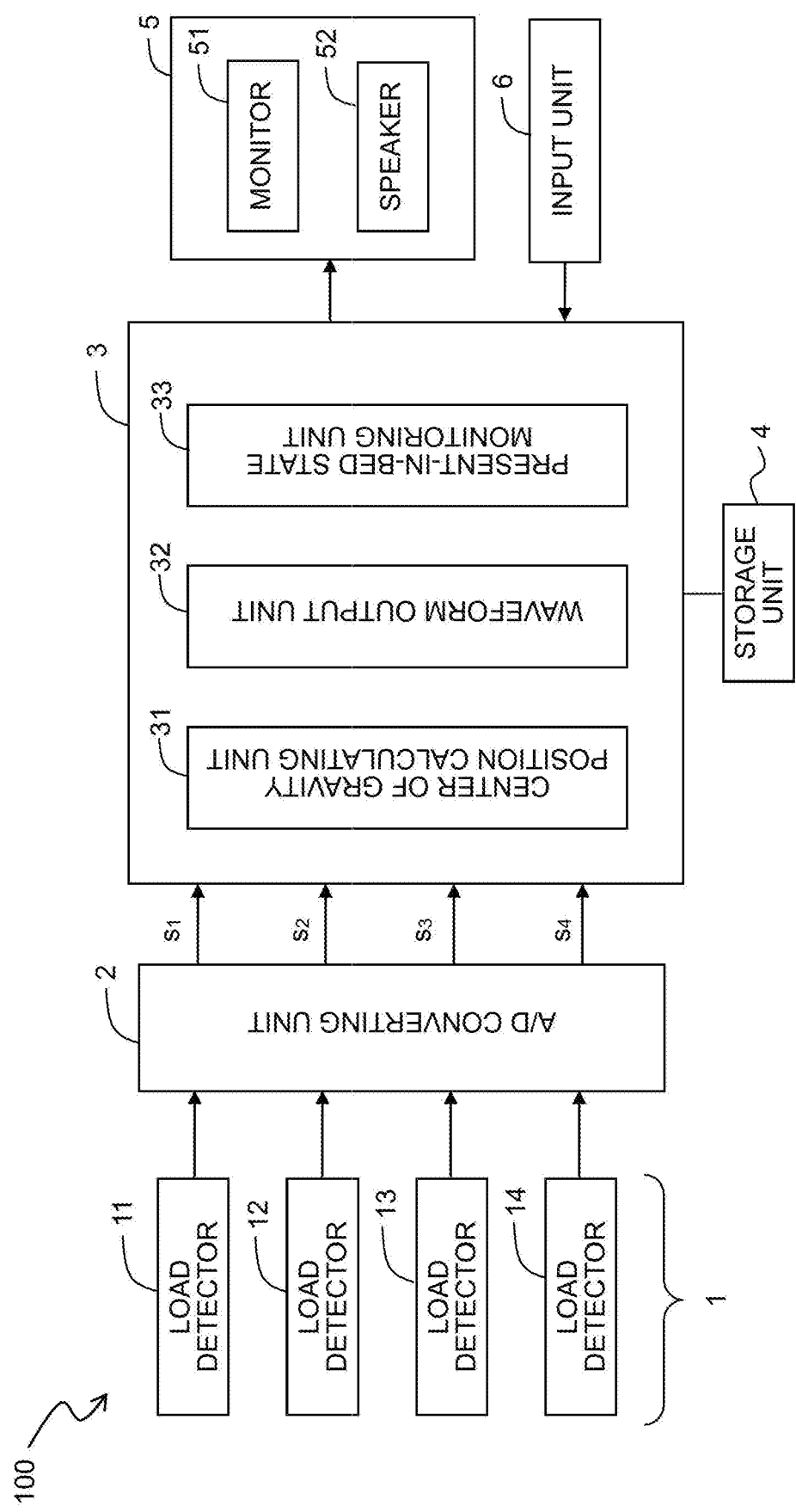
FIG. 1 is a block diagram depicting a configuration of a present-in-bed state monitoring system according to an embodiment of the present invention.

As shown in FIG. 1, a present-in-bed state monitoring system 100 of this embodiment primarily has a load detecting unit 1, a control unit 3, a storage unit 4, and a notifying unit 5. The load detecting unit 1 and the control unit 3 are connected via an A/D converting unit 2. The control unit 3 is further connected to an input unit 6.

The load detecting unit 1 includes four load detectors 11, 12, 13, and 14. Each of the load detectors 11, 12, 13, and 14 is a load detector for detecting a load by using, for example, a beam-type load cell. Such a load detector is disclosed, for example, in Japanese Patent No. 4829020 and Japanese Patent No. 4002905. Each of the load detectors 11, 12, 13, and 14 is connected to the A/D converting unit 2 by way of wiring.

Figure 2:
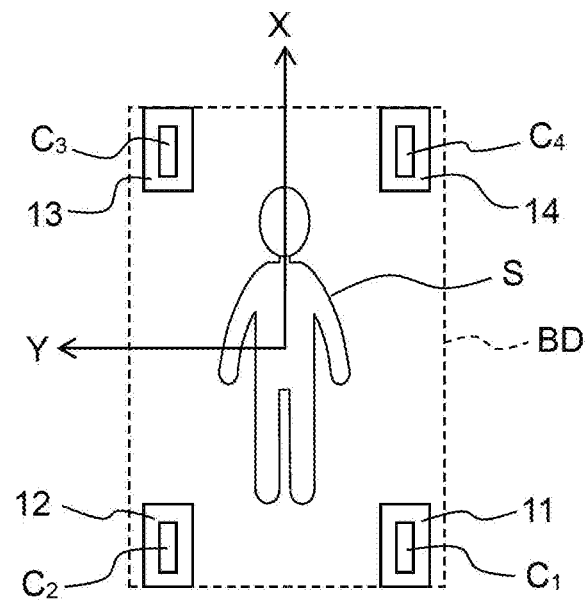
FIG. 2 is an illustrative view depicting an arrangement of load detectors for a bed.

The four load detectors 11, 12, 13, and 14 of the load detecting unit 1 are arranged under legs of a bed used by a subject. In particular, as depicted in FIG. 2, the load detectors 11, 12, 13, and 14 are arranged respectively under casters $C_1$, $C_2$, $C_3$, and $C_4$ fitted on the lower ends of the legs at the four corners of the bed BD.

The A/D converting unit 2 includes an A/D convertor connected respectively to the load detecting unit 1 and the control unit 3 by way of wiring, to convert analog signals from the load detecting unit 1 to digital signals.

The control unit 3 is a dedicated or general-purpose computer inside which a center of gravity position calculating unit 31, a waveform output unit 32, and a present-in-bed state monitoring unit 33 are constructed.

The storage unit 4 is a storage device for storing data used in the present-in-bed state monitoring system 100 and, for example, can use a hard disk (magnetic disk) for that purpose. The notifying unit 5 includes a monitor 51 such as a liquid crystal monitor or the like for visual (image) notification on the basis of the output from the control unit 3, and a speaker 52 for auditory notification also on the basis of the output from the control unit 3.

The input unit 6 is an interface for performing predetermined inputs for the control unit 3, which may be a keyboard and a mouse.

An explanation will be made on an operation of monitoring the present-in-bed state of the subject on the bed by using such present-in-bed state monitoring system 100. In this context, to monitor the present-in-bed state of the subject is, in particular for example, to monitor whether or not the subject is in a condition of a possible tumble or fall from the bed (to be referred to below as "dangerous condition" as appropriate).

Figure 3:
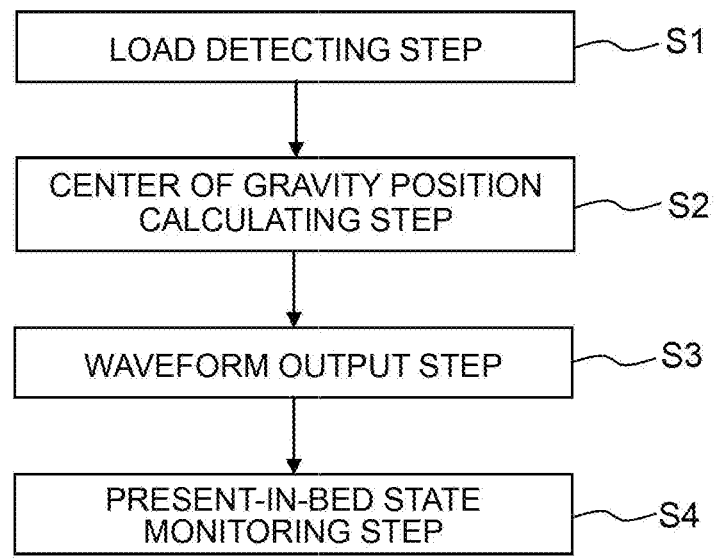
FIG. 3 is a flow chart depicting a method for monitoring a present-in-bed state by using the present-in-bed state monitoring system.

Monitoring the present-in-bed state of the subject by using the present-in-bed state monitoring system 100 primarily includes: as depicted in the flow chart of FIG. 3, a load detecting step S1 for detecting the (body weight) load of the subject; a center of gravity position calculating step S2 for obtaining (finding) a center of gravity position of the subject on the basis of the detected load; a waveform output step S3 for outputting a waveform including a respiratory waveform (to be described later on) on the basis of a temporal variation of the center of gravity position of the subject; and a present-in-bed state monitoring step S4 for monitoring the present-in-bed state of the subject by using the center of gravity position of the subject and the waveform including the respiratory waveform of the subject.

[The Load Detecting Step]

In the load detecting step S1, the load detectors 11, 12, 13, and 14 are used to detect the load of the subject S on the bed BD. Because the load detectors 11, 12, 13, and 14 are arranged respectively under the casters $C_1$, $C_2$, $C_3$, and $C_4$, the load applied on the upper surface of the bed BD is detected dispersively by the four load detectors 11, 12, 13, and 14.

Each of the load detectors 11, 12, 13, and 14 detects the load (a variation in load), and outputs the result as an analog signal to the A/D converting unit 2. The A/D converting unit 2 converts the analog signal into a digital signal through a sampling period of 5 milliseconds, for example, and then outputs the digital signal (to be referred to below as "load signal") to the control unit 3. Hereinafter, the term "load signals $s_1$, $s_2$, $s_3$, and $s_4$" will be used to refer respectively to the load signals obtained by way of the A/D converting unit 2 converting the analog signals outputted from the load detectors 11, 12, 13, and 14 into the digital format.

[Center of Gravity Position Calculating Step]

In the center of gravity position calculating step S2, the center of gravity position calculating unit 31 calculates the position G (X, Y) of the center of gravity G of the subject S on the bed BD at a predetermined period T (for example, a period equal to the sampling period of 5 milliseconds described above) on the basis of the load signals $s_1$ to $s_4$ fed from the load detectors 11 to 14 to obtain the position of the center of gravity G of the subject S, and the temporal variation thereof (center of gravity locus). In this case, (X, Y) indicates the coordinates on the XY coordinate plane in which the X-axis extends in the longitudinal direction of the bed BD and the Y-axis extends in the lateral direction of the bed BD while the central portion of the bed BD is the origin (FIG. 2).

The calculation of the position G (X, Y) of the center of gravity G by the center of gravity position calculating unit 31 is performed in accordance with the following operation. That is, G (X, Y) is calculated in accordance with the following formulas assuming that the coordinates of the load detectors 11, 12, 13, and 14 are $(X_{11}, Y_{11})$, $(X_{12}, Y_{12})$, $(X_{13}, Y_{13})$, and $(X_{14}, Y_{14})$ respectively, and the detection values of the load detectors 11, 12, 13, and 14 are $W_{11}$, $W_{12}$, $W_{13}$, and $W_{14}$ respectively.

$$X = \frac{X_{11} \times W_{11} + X_{12} \times W_{12} + X_{13} \times W_{13} + X_{14} \times W_{14}}{W_{11} + W_{12} + W_{13} + W_{14}} \quad \text{[Formula 1]}$$

$$Y = \frac{Y_{11} \times W_{11} + Y_{12} \times W_{12} + Y_{13} \times W_{13} + Y_{14} \times W_{14}}{W_{11} + W_{12} + W_{13} + W_{14}} \quad \text{[Formula 2]}$$

The center of gravity position calculating unit 31 obtains the position G (X, Y) of the center of gravity G, and the temporal variation thereof, i.e., the center of gravity locus after calculating the position G (X, Y) of the center of gravity G at the predetermined sampling period T on the basis of the formulas 1 and 2 described above. The result is stored, for example, in the storage unit 4.

[Waveform Output Step]

In the waveform output step S3, the waveform output unit 32 draws the waveform including the respiratory waveform of the subject S on the basis of the center of gravity locus.

Here, in the present specification and the present invention, the term "respiratory waveform" refers to a waveform exhibiting a respiratory state of the subject S, where time is denoted on the horizontal axis while the depth of respiration is denoted on the vertical axis. An example of the respiratory waveform is a respiratory waveform W depicted in FIG. 4B.

In the respiratory waveform W, the point $W_{max}$ denoting the depth at the maximum value corresponds to the point of time when the subject S ends an expiration (or an inspiration), whereas the point $W_{min}$ denoting the depth at the minimum value corresponds to the point of time when the subject S ends an inspiration (or an expiration). One period of the respiratory waveform W corresponds to one cycle of the respiration.

Based on an observation of the respiratory waveform W, it is possible to obtain such information about the subject S as the respiratory rate, respiratory state (stable respiration, occurrence of snore, occurrence of apnea, utterance, and the like), respiratory capacity (or breathing capacity, or tidal volume), and the like.

The respiratory waveform is outputted on the basis of the flowing principle.

The respiration of human is performed by moving the chest and the diaphragm to expand and shrink the lungs. In this context, when the air is inhaled (or an inspiration is performed), i.e., when the lungs are expanded, the diaphragm is lowered downwardly, and the internal organs are also moved downwardly. On the other hand, when the air is expired (or an expiration is performed), i.e., when the lungs are shrunk, the diaphragm is raised upwardly, and the internal organs are also moved upwardly. The inventors of the present invention have found out, from a research on the respiration, that the center of gravity of the subject vibrates approximately along the up/down direction of the subject (the backbone direction), i.e., along the body axis direction, due to the up/down movement of the internal organs in accordance with the respiration.

Figure 4B:
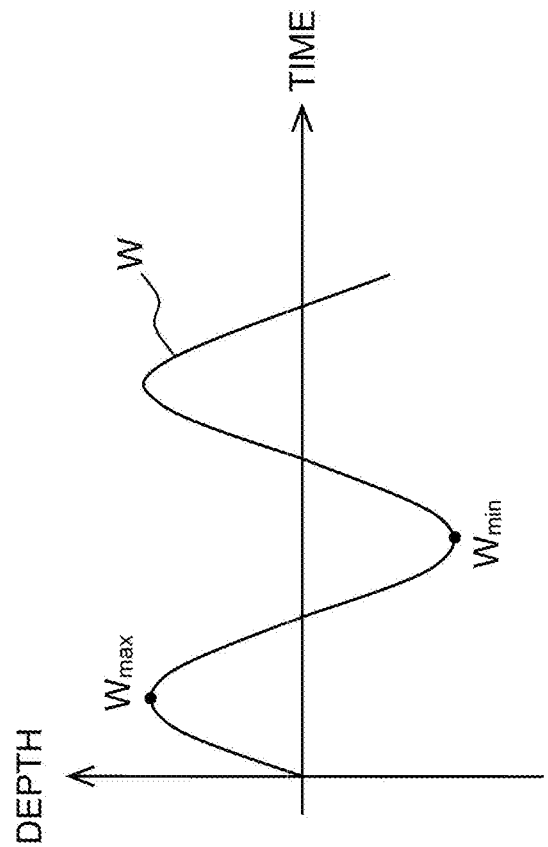
FIG. 4B depicts an example of a respiratory waveform drawn on the basis of the respiratory oscillation.
Figure 4A:
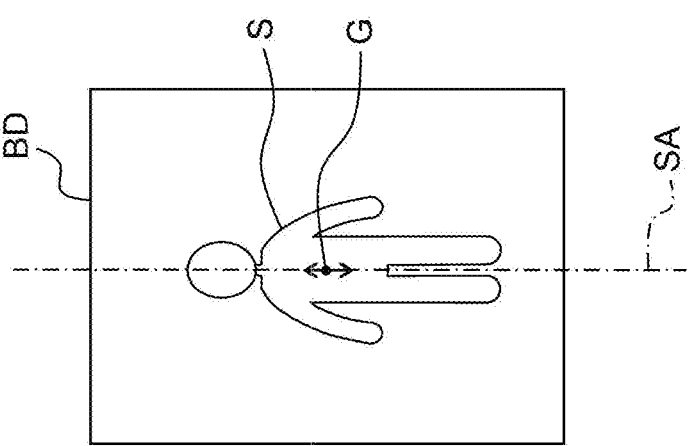
FIG. 4A is an illustrative view depicting a body axis of a subject, and an aspect of respiratory oscillation (vibration) along a body axis direction.

In the following description, the term "respiratory oscillation (vibration)" is used to refer to such a vibration or oscillation along the body axis direction of the subject in accordance with the respiration of the subject. As depicted in FIG. 4A with two arrows, the center of gravity G of the subject S oscillates along the direction of the body axis SA of the subject S due to the respiratory oscillation.

In particular, for example, the respiratory waveform can be obtained by plotting the locus of the respiratory oscillation on a temporal area. That is, the respiratory waveform W of the subject S is outputted by plotting the locus of the respiratory oscillation of the subject S on a graphic area with the horizontal axis as the time axis and with the vertical axis as the direction of the body axis SA of the subject S.

In the present-in-bed state monitoring system 100 of this embodiment, in particular, the waveform output unit 32 outputs the waveform including the respiratory waveform W of the subject S in the following manner. The waveform including the respiratory waveform W refers to a waveform including the respiratory waveform W, and a part deviating from the respiratory waveform due to a body motion of the subject (to be described in detail later on).

The waveform output unit 32 outputs the waveform including the respiratory waveform W of the subject S, based on the movement of the center of gravity G of the subject S.

The respiratory waveform W is outputted in a period when it is possible to catch the respiratory oscillation of the center of gravity G. The center of gravity G also moves due to body motions of the subject S other than the respiration, and the displacement of the center of gravity G due to a body motion is far larger than the amplitude of the respiratory oscillation. Therefore, it is only possible to catch the respiratory oscillation, in practice, in a period when there are no body motion arising in the subject S (to be referred to below as "resting period" as appropriate), and the respiratory waveform is outputted in the resting period.

Based on the locus of the center of gravity G, the waveform output unit 32 starts to output the respiratory waveform at the point of catching the respiratory oscillation (at the start point of the resting period), or in particular for example, at the point of having continuously observed the peaks. The respiratory waveform is outputted with a peak of the respiratory oscillation as the reference. Therefore, when there is a change in the amplitude of the respiratory oscillation due to some change or the like in the respiratory state of the subject, the center of the respiratory waveform does not shift but, on the other hand, the change in the amplitude is reflected.

If there is a body motion arising in the subject S, then a deviation from the respiratory waveform occurs at that point (the end point of a resting period). Then, when another resting period comes, outputting the respiratory waveform W is started again.

The waveform output unit 32 may draw the outputted respiratory waveform W on the monitor 51 of the notifying unit 5.

[Present-In-Bed State Monitoring Step]

In the present-in-bed state monitoring step S4, the present-in-bed state monitoring unit 33 monitors the present-in-bed state of the subject S, based on the position of the center of gravity G calculated in the center of gravity position calculating step S2, and the waveform including the respiratory waveform W drawn in the waveform output step S3.

Figure 5:
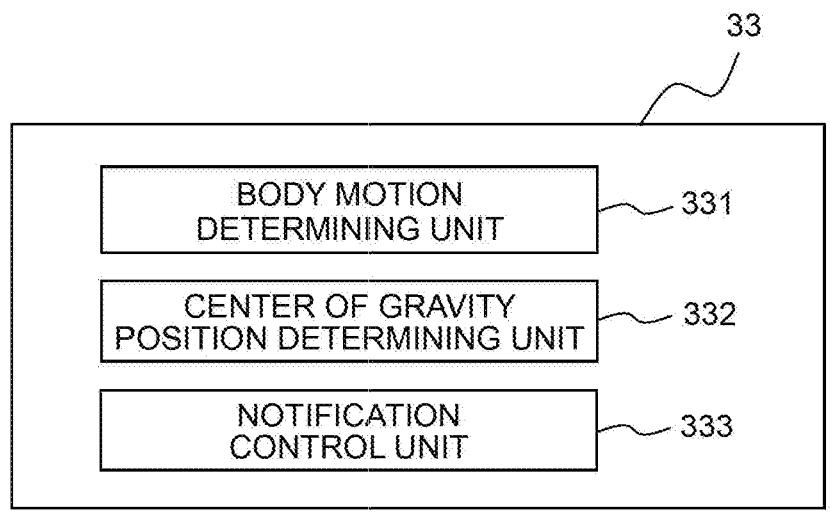
FIG. 5 is a block diagram depicting a configuration of a present-in-bed state monitoring unit.

As depicted in FIG. 5, the present-in-bed state monitoring unit 33 includes a body motion determining unit 331, a center of gravity position determining unit 332, and a notification control unit 333.

As depicted in FIG. 6, the present-in-bed state monitoring step S4 includes a body motion determining step S41 for determining whether or not the subject S has a body motion, a center of gravity position determining step S42 for determining whether or not the center of gravity of the subject S is in a bed edge area, a first notifying step S43 to be carried out when the subject S has a body motion and the center of gravity of the subject S is in the bed edge area, and a second notifying step S44 to be carried out when the subject S does not have a body motion but the center of gravity of the subject S is in the bed edge area.

In the body motion determining step S41, the body motion determining unit 331 determines whether or not the subject S has a body motion, based on the waveform including the respiratory waveform W of the subject S.

Here, a body motion of the subject S refers to a body movement of the subject which is different from the respiration. In particular, the body motion includes a "large body motion" and a "small body motion".

In this specification and in the present invention, the "large body motion" refers to a comparatively large one in the body motion of the subject, along with a torso (trunk, body-trunk) motion such as, in particular, a turn-over, get-up or the like. If the subject performs a large body motion, then generally speaking, the subject's body axis changes in orientation (orientation of the extending backbone of the subject).

If the large body motion is defined from such a view of point as exhibiting a temporal variation of the position of the center of gravity, then generally it is possible to define the large body motion as a movement of the center of gravity through a comparatively long distance which is longer than a predetermined distance within a predetermined period, that is, a body motion where the center of gravity moves at a comparatively high speed. In particular, for example, it is possible to define the large body motion as a body motion where the movement of the center of gravity occurs at a speed exceeding a predetermined value V. Alternatively, on the basis of the difference from the temporal variation of the position of center of gravity arising from the small body motion, for example, it is also possible to define the large body motion as a body motion to move the center of gravity through a distance longer than a predetermined multiple of the distance of the movement of the center of gravity due to the small body motion within a predetermined length of time. Further, it may also be defined by way of comparison to the amplitude of the respiratory oscillation. In particular for example, it is possible to define such a body motion as the large body motion as to give rise to a movement of the center of gravity which exceeds a predetermined multiple of the amplitude of the respiratory oscillation (the respiratory waveform) in a predetermined period.

In this specification and in the present invention, the "small body motion" refers to a comparatively small one in the body motion of the subject, without the torso (trunk, body-trunk) motion such as, in particular, the mere motion of a hand, a foot, the head, and/or the like.

If the small body motion is defined from such a view of point as exhibiting a temporal variation of the position of the center of gravity, then generally it is possible to define the small body motion as a movement of the center of gravity through a comparatively short distance within a predetermined length of time, that is, a body motion where the center of gravity moves at a comparatively low speed. In particular, for example, it is possible to define the small body motion as a body motion where the movement of the center of gravity occurs at a speed of a predetermined value v or so. Further, it may also be defined by way of comparison to the amplitude of the respiratory vibration. In particular for example, it is possible to define such a body motion as the small body motion as to give rise to a movement of the center of gravity which is about a predetermined multiple of the amplitude of the respiratory oscillation (the respiratory waveform) in a predetermined period. Further, the small body motion may also be defined as a body motion giving rise to a movement of the center of gravity excluding the oscillation in a certain direction, among the movements of the center of gravity which fit into above definitions. According to such a definition, when the movement of the center of gravity is focused on, it is possible to more clearly distinguish the small body motion from the respiration.

The following principle is applied to the determination of whether or not there is a body motion on the basis of the waveform including the respiratory waveform.

In the waveform output step S3, the waveform output unit 32 outputs the respiratory waveform W based on the respiratory oscillation of the center of gravity G of the subject S, that is, the oscillation of the center of gravity G in the direction of the body axis S. Therefore, if the subject S has a body motion and the center of gravity G of the subject S moves through a longer distance than the amplitude of the respiratory oscillation, then the deviation from the respiratory waveform W arises and, as depicted in FIGS. 7A and 7B, the amplitude of the waveform including the respiratory waveform W becomes large temporally.

Figure 7A:
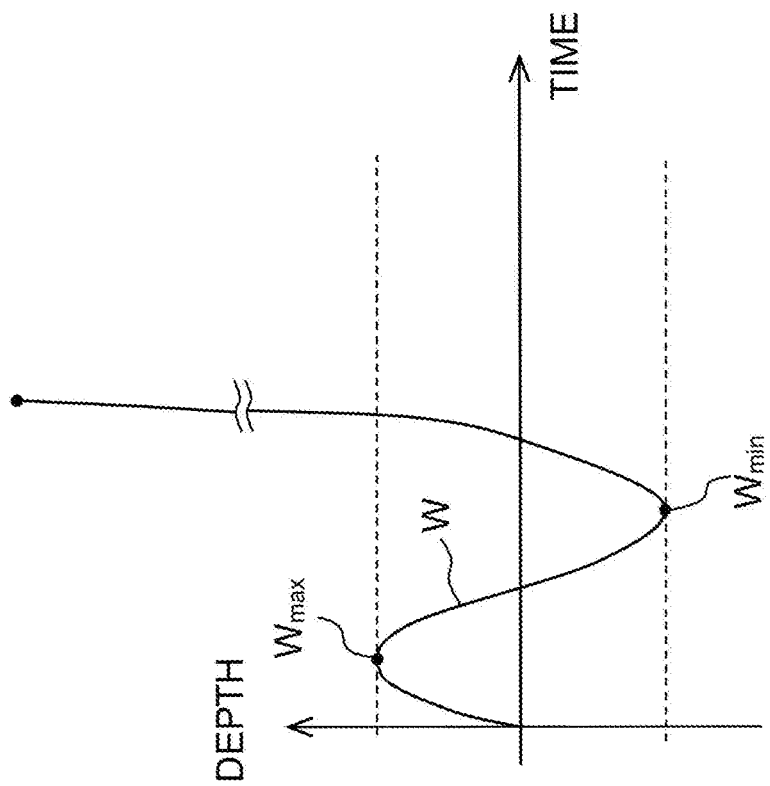
FIG. 7A depicts an example of waveform including a respiratory waveform when a small body motion arises in the subject.
Figure 7B:
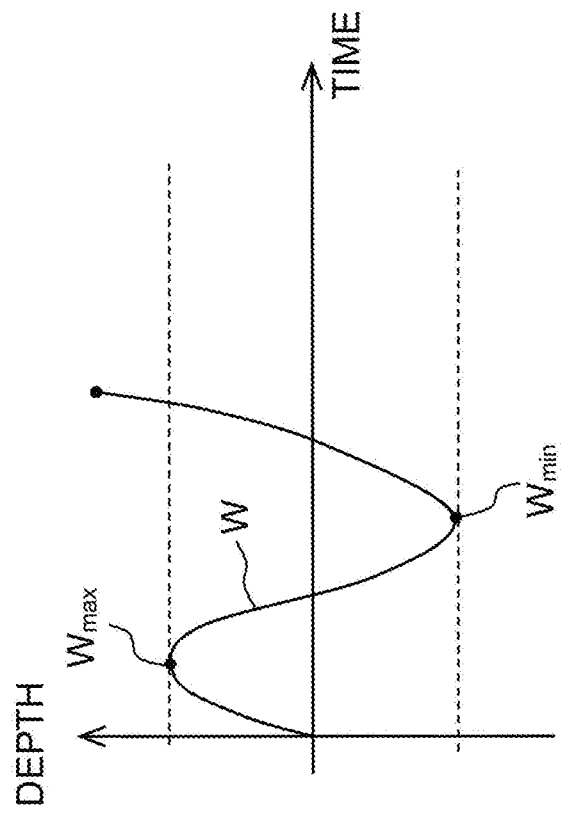
FIG. 7B depicts an example of waveform including a respiratory waveform when a large body motion arises in the subject.
Figure 8:
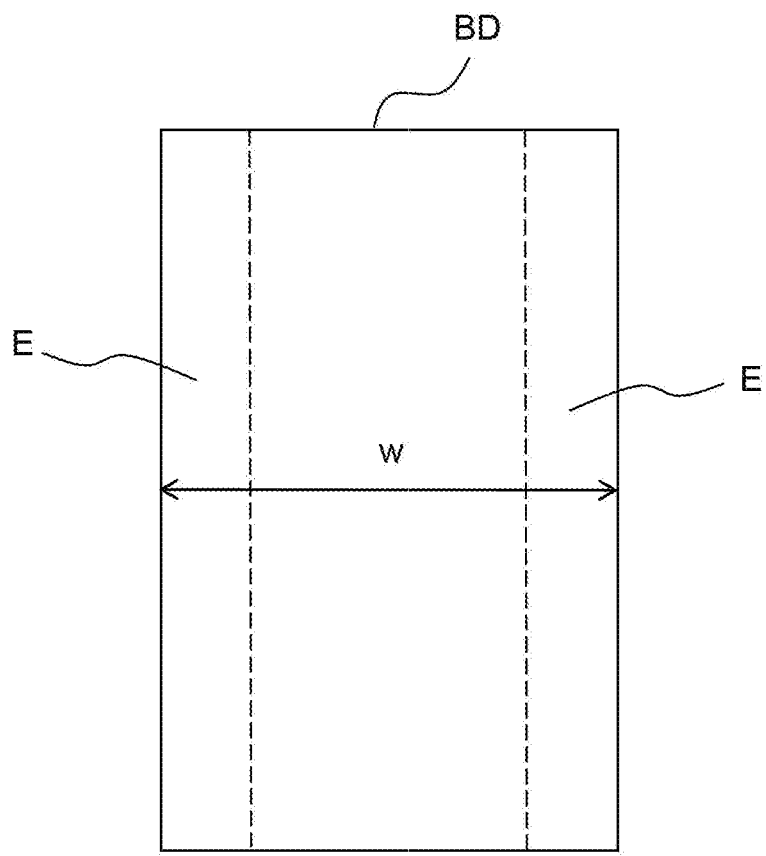
FIG. 8 depicts an example of bed edge areas set on the bed BD.

FIG. 7A depicts an aspect of waveform including the respiratory waveform W when a small body motion arises in the subject S. FIG. 7B depicts an aspect of waveform including the respiratory waveform W when a large body motion arises in the subject S. If a small body motion arises in the subject S, then the amplitude of the waveform including the respiratory waveform W is larger than that of the respiratory waveform W during the resting period, whereas if a large body motion arises in the subject S, then the amplitude of the waveform including the respiratory waveform W is even larger than that of the respiratory waveform W when a small body motion arises in the subject.

The body motion determining unit 331 observes the waveform including the respiratory waveform W, and determines that a body motion (either a small body motion or a large body motion) has arisen in the subject S, based on the fact that the amplitude of the waveform including the respiratory waveform W has become as large as exceeds a predetermined ratio in comparison with the amplitude of the respiratory waveform W during the resting period.

Further, generally speaking, a large body motion or a small body motion arises in the subject in an irregular manner or at a different period from that of the respiratory waveform W. Therefore, if a large body motion or a small body motion arises in the subject, then the waveform including the respiratory waveform W may have a different period from that of the respiratory waveform W or give rise to phasal deviation. Hence, based on the period or the phase of the waveform including the respiratory waveform W, it is possible for the body motion determining unit 331 to determine that a body motion has arisen in the subject.

In the body motion determining step S41, if it is determined that the subject S has a body motion, then the center of gravity position determining unit 332 carries out the center of gravity position determining step S42.

The center of gravity position determining unit 332 determines whether or not the center of gravity G of the subject S is in either one of edge areas E of the bed BD (FIG. 8) at the point when the subject S has a body motion. The width of either of the edge areas E may be set at any possible value.

If the center of gravity G of the subject S is determined as in either of the edge areas E in the center of gravity position determining step S42, then the notification control unit 333 carries out the first notifying step S43.

In the first notifying step S43, the notification control unit 333 notifies the user of the present-in-bed state monitoring system 100 via the notifying unit 5 that there is a high degree of risk of the subject S falling from the bed BD. In particular, for example, a red icon is lit up on the monitor 51 and an alarm sound is emitted via the speaker 52.

On the other hand, if the center of gravity G of the subject S is determined as not in either of the edge areas E in the center of gravity position determining step S42, then the body motion determining step S41 is carried out again.

Even if it is determined that the subject S has not had a body motion in the body motion determining step S41, the center of gravity position determining unit 332 still carries out the center of gravity position determining step S42. In this case, if the center of gravity position determining unit 332 determines that the center of gravity G of the subject S is in either of the edge areas E of the bed BD, then the notification control unit 333 carries out the second notifying step S44.

In the second notifying step S44, the notification control unit 333 notifies the user of the present-in-bed state monitoring system 100 via the notifying unit 5 that there is a possibility for the subject S to fall from the bed BD. In particular, for example, a yellow icon is lit up on the monitor 51 and a caution sound is emitted via the speaker 52 to give an impression of emergency at a lower level than the alarm sound emitted in the first notifying step S43.

According to the knowledge of the inventors of the present invention, the subject being asleep rarely falls from the bed whereas the subject being awake may fall from the bed usually due to failing in body control. Therefore, in the present-in-bed state monitoring system 100 of this embodiment, notification is performed to give an impression of emergency at a higher level for the first notifying step S43 carried out when there is a body motion arising in the subject S (that is, the subject S is presumed awake), than for the second notifying step S44 carried out when there is no body motion arising in the subject S (that is, the subject S is presumed asleep).

The effects of the present-in-bed state monitoring system of this embodiment are organized as follows.

The present-in-bed state monitoring system 100 of this embodiment monitors the present-in-bed state of the subject S not only by observing the position of the center of gravity G of the subject S but also by taking into consideration whether or not the subject S has a body motion, that is, whether or not the subject S is in a resting state. Therefore, it is possible to determine, with higher precision, that the subject S is at a risk of a possible fall or the like, and to inform the user of the present-in-bed state monitoring system 100 of that risk.

The present-in-bed state monitoring system 100 of this embodiment can perform two different types of notification such as alarm and caution via the notifying unit 5, according to the state of the subject S. Therefore, the user of the present-in-bed state monitoring system 100 can refer to the types of notification for taking suitable response without excessive reaction.

The present-in-bed state monitoring system 100 of this embodiment uses the waveform including the respiratory waveform W of the subject S for monitoring the present-in-bed state of the subject S. The respiratory waveform is outputted on the basis of the respiration of the subject or, in other words, it is not outputted if what is present on the bed is an inanimate object (such as a bag, baggage, or the like). Therefore, according to the present-in-bed state monitoring system 100 of this embodiment, unnecessary monitoring possibly performed when an inanimate object is placed on the bed, is prevented from being performed.

The present-in-bed state monitoring system 100 of this embodiment outputs the respiratory waveform containing a lot of information related to the respiratory state of the subject S, draws a graph for the same on the monitor 51, and uses the waveform including the respiratory waveform in determining whether or not the subject S has a body motion and, consequently, in monitoring the present-in-bed state of the subject S. That is, the present-in-bed state monitoring system 100 of this embodiment is configured to exhibit abundant respiratory information and monitor the present-in-bed state with high precision, efficiently with a simple system. Using this present-in-bed state monitoring system 100, the medical doctors and nurses can reliably observe the risk of fall from the bed while monitoring the respiratory stability and/or the respiratory state such as snores and the like of the subject S.

The present-in-bed state monitoring system 100 of this embodiment uses the load detectors 11 to 14 arranged under the legs of the bed BD to monitor the present-in-bed state of the subject S noninvasively. That is, with the present-in-bed state monitoring system 100 of this embodiment, it is not necessary to attach any measuring device to the body of the subject S so that the subject S will not feel discomfort and a sense of incongruity.

Modified Embodiments

It is possible to use the following modified embodiments with respect to the present-in-bed state monitoring system 100 of the above embodiment.

Figure 9:
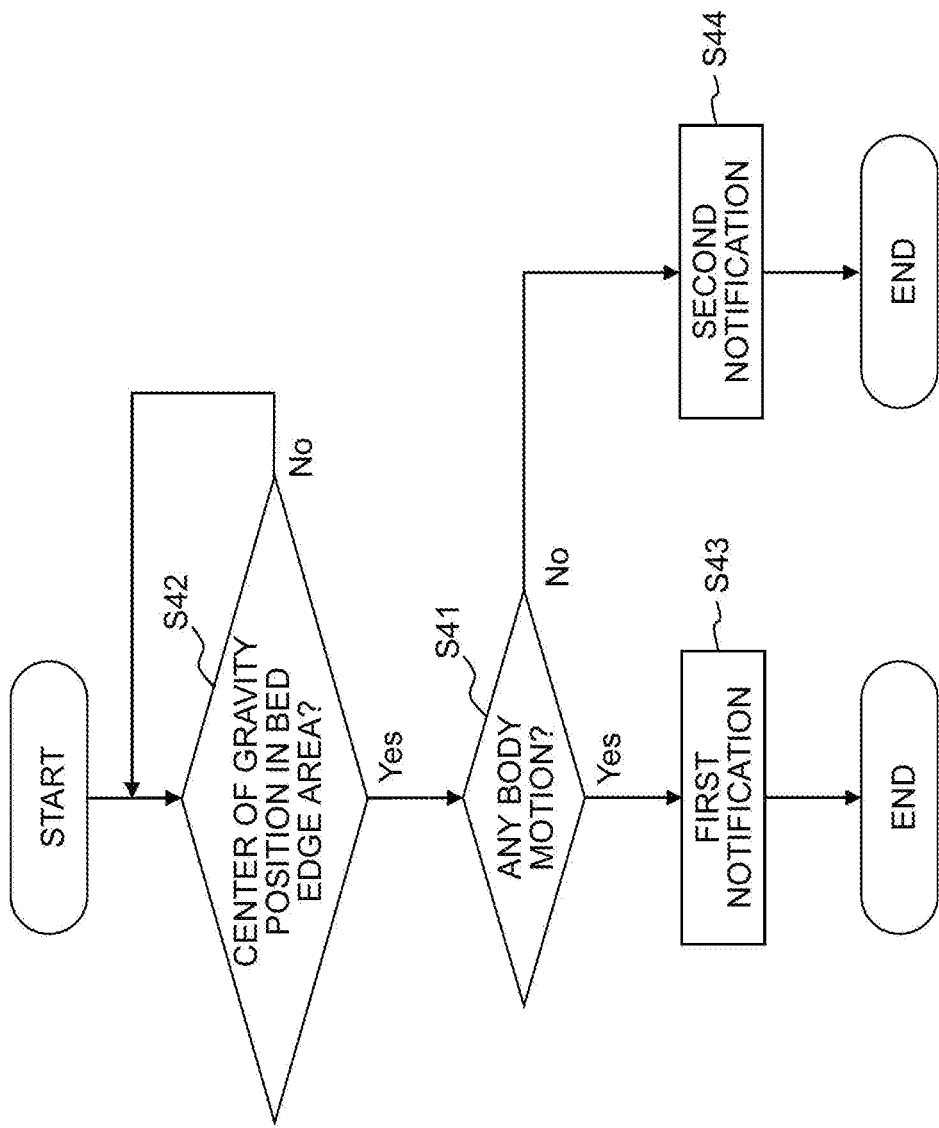
FIG. 9 is a flow chart depicting a procedure of a present-in-bed state monitoring step according to a modified embodiment of the present invention.

In the present-in-bed state monitoring system 100 of the above embodiment, the present-in-bed state monitoring unit 33 determines whether or not the center of gravity G of the subject S is in either of the edge areas E of the bed BD after firstly determining whether or not the subject S has a body motion. However, without being limited to that, as depicted in the flow chart of FIG. 9, the present-in-bed state monitoring unit 33 according to a modified embodiment carries out the body motion determining step S41 after carrying out the center of gravity position determining step S42.

In particular, the present-in-bed state monitoring unit 33 of the modified embodiment first carries out the center of gravity position determining step S42. Then, it carries out the body motion determining step S41 if the center of gravity G of the subject S is in either of the edge areas E, or carries out the center of gravity position determining step S42 again if the center of gravity G of the subject S is in neither of the edge areas E. If it is determined that the subject S has a body motion in the body motion determining step S41, then the first notifying step S43 is carried out, whereas if it is determined that the subject S does not have a body motion in the body motion determining step S41, then the second notifying step S44 is carried out. As an example, the contents of the first and second notifying steps S43 and S44 are the same as in the above embodiment.

Further, the present-in-bed state monitoring unit 33 according to another modified embodiment may carry out the body motion determining step S41 and the center of gravity position determining step S42 at the same time. The present-in-bed state monitoring unit 33 of another modified embodiment carries out the first notifying step S43 if it is determined that the center of gravity G of the subject S is in either of the edge areas E of the bed BD and the subject S has a body motion, or carries out the second notifying step S44 if it is determined that the center of gravity G of the subject S is in either of the edge areas E of the bed BD and the subject S does not have a body motion.

In the present-in-bed state monitoring system 100 of the above embodiment, the body motion determining unit 331 of the present-in-bed state monitoring unit 33 determines that the subject S has a body motion if the subject S has either a small body motion or a large body motion. However, without being limited to that, the body motion determining unit 331 may determine that the subject S has a body motion only when the subject S has a large body motion.

For subject in some conditions (symptoms and the like), a distinguish of the contents of notification based on the present-in-bed state of the subject S (for example, the degree of likelihood to fall) can be performed more appropriately, by distinguishing carrying out the first notifying step S43 to perform the first notification and carrying out the second notifying step S44 to perform the second notification based on whether or not there is a large body motion arising in the subject S as in the above manner.

Based on the waveform including the respiratory waveform W, for example, the body motion determining unit 331 of this modified embodiment may determine that there is a large body motion arising in the subject S if the amplitude of the waveform including the respiratory waveform W becomes as large as exceeds a predetermined ratio in comparison with the amplitude of the respiratory waveform W during the resting period.

Note that in the waveform output step S3, when the waveform output unit 32 outputs the respiratory waveform W, a bandpass filter may be used to cancel the influence of movement of the center of gravity G corresponding to a small body motion. By virtue of this, it is possible to output the respiratory waveform W without receiving the influence of a small body motion, thereby allowing for determining whether or not there is a large body motion with higher precision, on the basis of the waveform including the respiratory waveform W.

The notification control unit 333 of the present-in-bed state monitoring unit 33 of the above embodiment carries out a display in the first notifying step S43 to give an impression of emergency at a higher level than in the second notifying step S44. However, without being limited to that, the notification control unit 333 may carry out a notification in the second notifying step S44 to give an impression of emergency at a higher level than in the first notifying step S43. Further, according to the condition of the subject S, it is possible to set other proper forms of notification for the first and second notifying steps S43 and S44.

Further, depending on the condition of the subject S (symptoms and the like), for example, it may be sufficient to perform a predetermined notification only if the center of gravity position of the subject S is in either of the edge areas E of the bed BD and there is a body motion arising in the subject S. Therefore, in the present-in-bed state monitoring system 100 of the above embodiment, the second notifying step S44 may be a step in which no notification is performed at all (that is, the second notifying step S44 may be omitted). Alternatively, the first notifying step S43 may be a step in which no notification is performed at all.

In the present-in-bed state monitoring system 100 of the above embodiment, the present-in-bed state monitoring unit 33 may have a present-in-bed determining unit for determining whether or not the subject is present on the bed (present-in-bed determination) on the basis of whether or not the respiratory waveform is outputted. In this case, the present-in-bed state monitoring unit 33 determines whether or not the subject is present with the present-in-bed determining unit and, if the subject is determined as present on the bed, then the present-in-bed state monitoring step S4 may be started.

In the present-in-bed state monitoring system 100 of the above embodiment, the load detectors 11, 12, 13, and 14 are not limited to load sensors using beam-type load cells but, for example, force sensors are also usable.

In the present-in-bed state monitoring system 100 of the above embodiment, the number of load detectors is not limited to four. It is also allowable to use five or more load detectors by providing an additional leg or additional legs for the bed BD. Alternatively, it is also allowable to arrange load detectors for only three of the legs of the bed BD. Even when three load detectors are used, it is still possible to detect the position of the center of gravity G of the subject S on the plane of the bed BD provided that the three load detectors are not arranged on a straight line.

Figure 10:
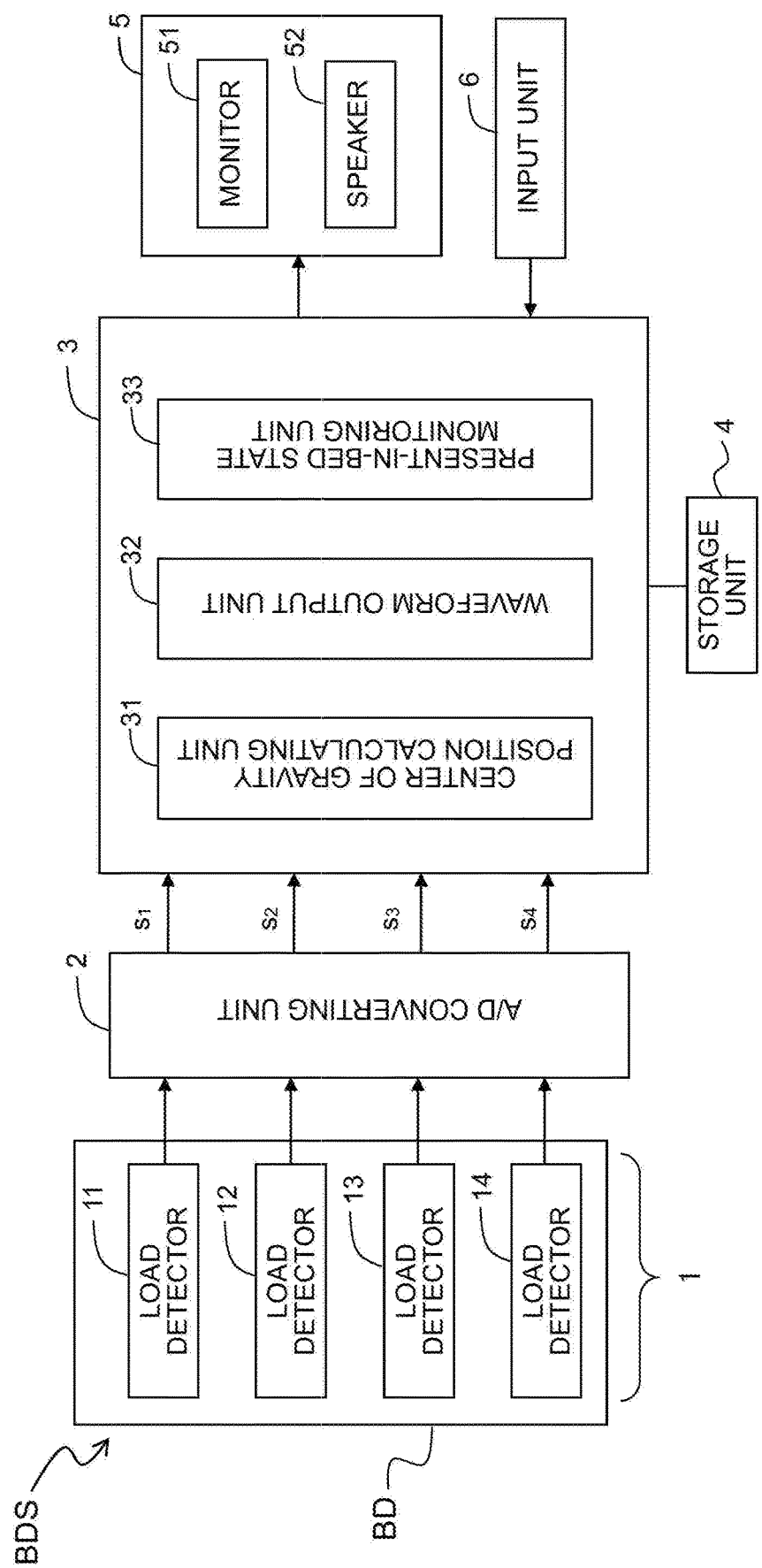
FIG. 10 is a block diagram depicting an overall configuration of a bed system according to another modified embodiment of the present invention.

In the present-in-bed state monitoring system 100 of the above embodiment, the load detectors 11, 12, 13, and 14 are arranged respectively under the casters $C_1$, $C_2$, $C_3$, and $C_4$ attached to the lower ends of the legs of the bed BD. However, there is no limitation thereto. Each of the load detectors 11, 12, 13, and 14 may be provided respectively between one of the four legs of the bed BD and the board of the bed BD. Alternatively, if each of the four legs of the bed BD can be divided into upper and lower portions, then each of the load detectors 11, 12, 13, and 14 may be provided between the upper portion of a leg and the lower portion of the leg. Further alternatively, the load detectors 11, 12, 13, and 14 may be formed integrally with the bed BD to construct a bed system BDS comprising the bed BD and the present-in-bed state monitoring system 100 of this embodiment (FIG. 10). Note that in this specification, the "load detectors provided on the bed" mean the load detectors each of which is provided between one of the four legs of the bed BD and the board of the bed BD as described above or the load detectors each of which is provided between the upper portion of one leg and the lower portion of the one leg.

In the present-in-bed state monitoring system 100 of the above embodiment, it is also allowable to provide a signal amplifying unit for amplifying the load signal fed from the load detecting unit 1 and/or a filtering unit for removing noises from the load signal, between the load detecting unit 1 and the A/D converting unit 2.

In the present-in-bed state monitoring system 100 of the above embodiment, the notifying unit 5 may include either the monitor 51 or the speaker 52. Further, the notifying unit 5 may include a printer for printing out the respiratory waveform, a simplified visual display means such as lamps for performing the first and second notifications, and/or the like, instead of the monitor 51 or in addition to the monitor 51. Further, the notifying unit 5 may include a vibration generating unit for performing the notification by way of vibration, instead of the speaker 52 or in addition to the speaker 52.

The present invention is not limited to the embodiment described above provided that the feature of the present invention is maintained. Other embodiments, which are conceivable within the scope of the technical concept of the present invention, are also included in the scope of the present invention.

INDUSTRIAL APPLICABILITY

According to the present-in-bed state monitoring system of the present invention, based on the detection of the load value of the subject, it is possible to monitor not only the respiratory state but also the present-in-bed state of the subject, with high precision and in a noninvasive manner. Therefore, if the system is used in hospitals, caregiving facilities and the like, then it is possible to preferably prevent the subject such as an inpatient, a caregiving facility resident, or the like from falling from the bed without giving the user any excessive burden and without giving the subject any discomfort.

PARTS LIST

1: load detecting unit, 11, 12, 13, 14: load detector, 2: A/D converting unit, 3: control unit, 31: center of gravity position calculating unit, 32: waveform output unit, 33: present-in-bed monitoring unit, 4: storage unit, 5: display unit, 51: monitor, 52: speaker, 6: input unit, 100: present-in-bed state monitoring system, BD: bed, BDS: bed system, S: subject.

The invention claimed is:

1. A present-in-bed state monitoring system configured to monitor a present-in-bed state of a subject on a bed, the system comprising:
a plurality of load detectors configured to be provided on the bed or under legs of the bed to detect a load of the subject;
a controller configured to control the present-in-bed state monitoring system to:
calculate a center of gravity position of the subject based on the detected load of the subject;
output a respiratory waveform of the subject based on a temporal variation of the calculated center of gravity position, the respiratory waveform having an amplitude corresponding to a depth of a respiration of the subject;
determine whether or not the center of gravity position is in an edge area of the bed; and
determine whether or not the subject has a body motion based on the respiratory waveform of the subject, the body motion being different from the respiration of the subject and causing a movement of the center of gravity position of the subject larger than a movement of the center of gravity position of the subject caused by the respiration of the subject, the controller determining that the subject has the body motion in a case that an amplitude of the respiratory waveform of the subject exceeds the amplitude of the respiratory waveform corresponding to the depth of the respiration of the subject; and
a notifying unit configured to perform a notification about the present-in-bed state of the subject based on a determination result of the determining of whether or not the subject has the body motion and a determination result of the determining of whether or not the center of gravity position is in the edge area of the bed,
wherein the controller is further configured to cause the notifying unit to perform the notification based on the determination result of the determining of whether or not the subject has the body motion and the determination result of the determining of whether or not the center of gravity position is in the edge area of the bed,
wherein the controller causes the notifying unit to perform a first notification in a case that the center of gravity position is determined to be in the edge area of the bed and the subject has determined to have the body motion, and causes the notifying unit to perform a second notification different from the first notification in a case that the center of gravity position is determined to be in the edge area of the bed and the subject is determined not to have the body motion,
wherein each of the first notification and the second notification is configured to indicate a degree of risk of the subject falling from the bed, and
wherein the first notification is configured to indicate the degree of risk higher than the degree of risk indicated by the second notification, or the second notification is configured to indicate the degree of risk higher than the degree of risk indicated by the first notification.

2. The present-in-bed state monitoring system according to claim 1, wherein the controller determines whether or not the subject has a large body motion involving a movement of a trunk of the subject, and
the controller causes the notifying unit to perform the first notification in a case that the center of gravity position is determined to be in the edge area of the bed and the subject is determined to have the large body motion.

3. The present-in-bed state monitoring system according to claim 1, wherein the controller is further configured to determine whether or not the subject is present on the bed based on the respiratory waveform.

4. The present-in-bed state monitoring system according to claim 1, wherein the notifying unit includes a monitor configured to perform the notification by an image, and a speaker configured to perform the notification by an audio.

5. A bed system comprising:
a bed; and
the present-in-bed state monitoring system as defined in claim 1.

6. The present-in-bed state monitoring system according to claim 1, wherein the controller is further configured to obtain a respiratory rate of the subject based on the respiratory waveform of the subject.

* * * * *